United States Patent [19]

Logothetis et al.

[11] Patent Number: 4,790,924
[45] Date of Patent: Dec. 13, 1988

[54] METHOD OF FABRICATION OF AIR/FUEL SENSORS BASED ON ELECTROCHEMICAL PUMPING AND SENSORS MADE THEREBY

[75] Inventors: Eleftherios M. Logothetis, Birmingham, Mich.; William J. Kaiser, West Covina, Calif.; William C. Vassell, Birmingham, Mich.

[73] Assignee: Ford Motor Company, Dearborn, Mich.

[21] Appl. No.: 138,101

[22] Filed: Dec. 28, 1987

[51] Int. Cl.[4] ............................................. G01N 27/58
[52] U.S. Cl. ................................... 204/412; 156/652; 156/656; 156/657; 156/659.1; 156/662; 204/425
[58] Field of Search ............... 204/410, 412, 425, 426, 204/15; 156/650, 652, 656, 657, 659.1, 662

[56] References Cited

U.S. PATENT DOCUMENTS 4,668,374  5/1987  Bhagat et al. .................. 204/412
4,671,852  6/1987  Pyke ............................... 156/652

Primary Examiner—G. L. Kaplan
Attorney, Agent, or Firm—Lorraine S. Melotik; Roger L. May

[57] ABSTRACT

A method is disclosed for making planar oxygen-solid electrolyte sensors. The method involves coating the several layers onto a support, selectively etching an etchable layer to form areas wherein the electrode layers and electrolyte layers may be formed thereon and, finally, etching the etchable layer totally away in order to form a chamber therein.

16 Claims, 2 Drawing Sheets

METHOD OF FABRICATION OF AIR/FUEL SENSORS BASED ON ELECTROCHEMICAL PUMPING AND SENSORS MADE THEREBY

TECHNICAL FIELD

This invention relates to a method for making substantially identical, planar oxygen pumping devices by a batch technique.

BACKGROUND OF THE INVENTION

In recent years, there has been an increased demand forhigh temperature oxygen sensors, mainly for the monitoring and control of combustion processes, such as the combustion of hydrocarbons in an internal combustion engine. One device of this type widely used for automotive engine control is an electrochemical oxygen concentration cell, usually made of zirconia ($ZrO_2$). In the most common configuration of this device, the $ZrO_2$ electrolyte is in the form of a thimble with one side exposed to the combustion environment and the other exposed to air as a reference atmosphere. This device provides an EMF output which is proportional to the logarithm of the oxygen partial pressure in the combustion, environment. Such a cell is generally termed an oxygen concentration cell.

Despite its low sensitivity, this device is widely used on automobile engines to control and maintain the air-to-fuel mixture in the engine cylinders at the stoichiometric value. A stoichiometric mixture contains just enough oxygen to burn the fuel completely to carbon dioxide and water. The satisfactory operation of this device arises from the fact that the oxygen partial pressure in the product of combustion (exhaust gas) changes by many orders of magnitude as the air-to-fuel mixture is varied through the stoichiometric value.

On the other hand, for the purpose of reducing fuel consumption, it is generally desirable to operate internal combustion engines with "lean" air-to-fuel mixtures, which contain excess air. For these lean mixtures, the oxygen partial pressure after combustion exhibits only a small and gradual change with change in the air-to-fuel mixture. These small changes cannot be easily measured with the above-mentioned oxygen concentration type device. One approach for obtaining high sensitivity devices for use in lean air-to-fuel operation is to employ a so-called oxygen-pumping scheme. Such oxygen-pumping is based on the fact that if a current is passed through an oxygen-conducting electrolyte, (e.g. zirconia), oxygen is transferred (pumped) from one side of the electrolyte to the other. Several oxygen sensors based on this principle have been described in the prior art. Examples are those described in U.S. Pat. Nos. 3,923,624 to Beckman et al; 3,654,112 to Beckman et al; 3,907,657 to Heijne et al; and 3,698,384 to Jayes.

Recently, a series of U.S. patents to Hetrick and Hetrick et al. (U.S. Pat. Nos. 4,272,320; 4,272,330; and 4,272,331) describe an oxygen-pumping device that has improved characteristics over previously described devices, e.g., higher speed of response, lower sensitivity to temperature variations and independence from ambient total pressure changes. These features make this device particularly useful for automotive engine use. This device has two pieces of dense zirconia sealed together to form a cavity that communicates with the outside environment through one or more apertures. Electrodes are deposited on the inside and outside walls of each of the two sections of the device, thus forming an oxygen pumping cell and a sensing cell. Still another oxygen pumping sensor is disclosed in U.S. Pat. No. 4,487,680 to Logothetis et al. It is termed a planar oxygen pumping sensor and includes first and second oxygen ion conductive solid electrolyte material layers, the first electrolyte material layer having greater porosity than the second electrolyte material layer, and first, second and third electrodes. The first electrode is between the first electrolyte material layer and the second electrolyte material layer. The second electrode is on the first electrolyte material layer. The third electrode is on the second electrolyte material layer. In this planar oxygen pumping sensor, only three electrodes are required to form an oxygen pump and an oxygen sensor. The more porous first electrolyte layer material acts to provide an enclosed volume with an aperture for establishing an oxygen gas reference partial pressure, similar to the structure of devices disclosed in the Hetrick et al. patents mentioned above.

As discussed above, oxygen pumping sensors possess several advantages over oxygen sensors such as the oxygen concentration cell. These advantages are higher sensitivity and less temperature dependence, and less dependence (even none) on the absolute gas pressure. Compared to the oxygen concentration cell, the oxygen pumping sensors have the additional advantage of higher signal levels (volts compared to millivolts for the oxygen concentration cell) and generally lower sensitivity to electrode properties. On the other hand, the oxygen pumping devices need calibration. If structural dimensions of oxygen pumping devices could be controlled and reproduced accurately, the need for calibrating individual devices would be minimized or even eliminated, but for one such "standard" device. It would also be desirable if the devices could be of a design which afforded a very low impedance for the device and a fast response time. Still further, it would be desirable if the fabrication techniques could be simplified so as to make the devices by a "batch" technique which would lead to lower costs. These are some of the advantages this invention offers.

DISCLOSURE OF THE INVENTION

This invention is directed to a method of fabricating planar oxygen pumping devices by a batch technique and to the devices fabricated according to this method. The devices, when associated with external circuitry, are capable of measuring oxygen partial pressure in a high temperature environment, such as may be found in an automobile exhaust. The method of fabricating the devices comprises first providing a substantially uniform layer of a ceramic material in contact with a first surface of a substantially uniform layer of etchable material, e.g., a wafer of single crystal silicon. The first surface of the etchable material is in contact with an inner surface of the ceramic material. The layer of ceramic material may be provided either by depositing the ceramic material on the etchable material or depositing the etchable material on the ceramic material. Grooves are then formed in a second surface opposite the first surface of the etchable material by etching away, in a predetermined pattern, substantially parallel, rectangular solid strips of etchable material to expose corresponding, substantially parallel rectangular portions of the inner surface of the layer of the ceramic material and leave at least a first set of subtantially identical, substantially parallel, rectangular solid projecting strips of etchable material. A layer of first electrode material is deposited over at least a portion of a top surface of each of the first set of rectangular solid projecting strips and on at least a portion of a groove bottom surface adjacent each said rectangular solid projecting strips. The layer of electrode material extends laterally continuously from at least the middle of the top surface of each of the first set of the rectangular solid projecting strips to at least about the middle of the adjacent groove bottom. A cover layer of an oxygen-ion conductive electrolyte material is subsequently deposited on the surface of the first electrode material and any exposed (i) etchable material and (ii) inner surfaces of the ceramic material. A layer of second electrode material is then deposited over at least a portion of a top surface of the oxygen-ion conductive electrolyte material to form a layered article, the layer of second electrode material extending laterally continuously from at least the middle of the top surface of each of the first set of rectangular solid projecting strips to at least about the middle of an adjacent groove bottom. Then, the layered article is cut through in planes perpendicular to the plane of the layered article in a grid pattern comprising (a) cuts between adjacent ones of the first set of the rectangular solid projecting strips to expose for each one the first and second electrode material and (b) cuts along lines perpendicular to the first cuts to produce a plurality of individual structures. The next step of the method of this invention comprises etching away the remaining etchable material from the individual structures to form the devices. The method of this invention may comprise additional steps for depositing layers of third and forth electrode materials.

BRIEF DESCRIPTION OF THE DRAWINGS

FIG. 3 is a cross-sectional view of a single crystal silicon wafer.

FIG. 4 shwws a cross-sectional view of the silicon wafer of FIG. 3 having a layer of ceramic material deposited thereon.

FIG. 5 shows a cross-sectional view of the configuration of FIG. 4 having grooves formed in the silicon wafer thereof.

FIG. 6 shows a perspective view of FIG. 5.

FIG. 7 shows a cross-sectional view of the configuration of FIG. 6 having an electrode layer deposited on a portion thereof.

FIG. 8 shows a cross-sectional view of the structure of FIG. 7 having an oxygen-ion-conductive electrolyte material deposited as a cover layer thereon.

FIG. 9 shows a cross-sectional view of the structure of FIG. 8 having a second electrode layer deposited on a portion of the oxygen-ion conductive layer thereof to form a layered article.

FIG. 10 shows a cross-sectional view of the layered article of FIG. 9 after cutting along lines 66 of FIG. 9.

DETAILED DESCRIPTION OF THE INVENTION

Figure 1:
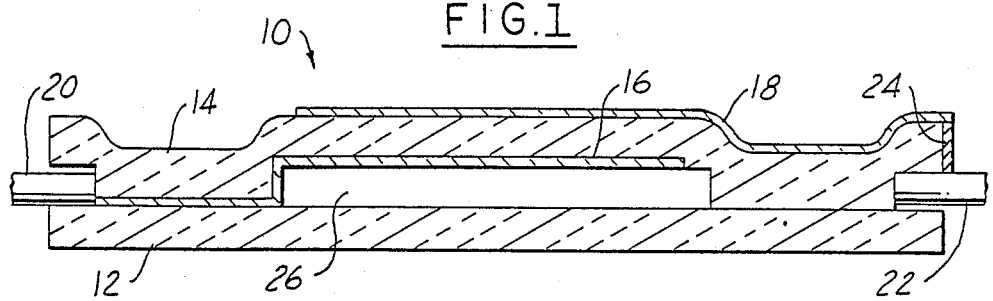
FIG. 1 is a cross-sectional view of an oxygen pumping device fabricated in accordance with a first embodiment of the method of this invention, wherein the device is a single-cell device.
Figure 2:
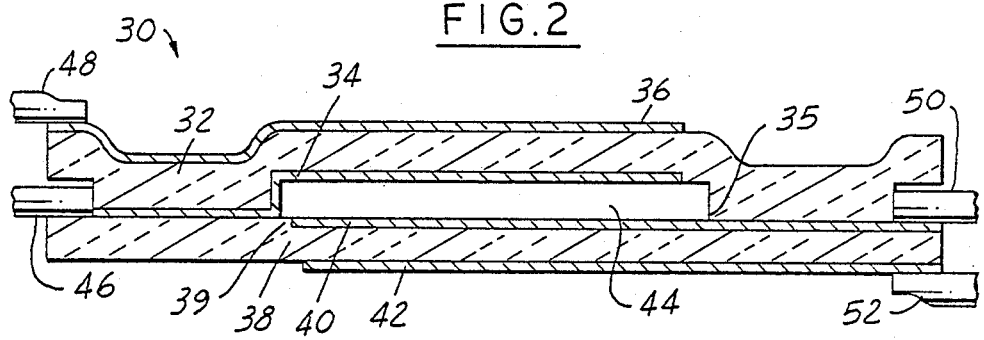
FIG. 2 is a cross-sectional view of an oxygen pumping device fabricated in accordance with a second embodiment of the method of this invention, wherein the device is a double-cell device.
Figure 3:
FIG. 3 through FIG. 10 depict the steps of the method of this invention for fabricating the device of FIG. 1.

This invention relates to a method for making substantially identical, planar oxygen pumping devices by a batch technique. The invention may be understood by refering to the drawings. FIG. 1 and FIG. 2 show cross-sectional views of constructions of embodiments of oxygen pumping devices produced by a method according to this invention. The FIG. 1 device (10) is one embodiment of a single-cell device while that of FIG. 2 is one embodiment of a double-cell device (30). In the FIG. 1 device (10), a layer (12) is composed of ceramic material and layer (14) is an oxygen-ion conductive electroylte material. A layer of first electrode material (16) and second electrode material (18) form reference electrodes in cont with the oxygen-ion conductive material (14). Cavity (36) is present in the device. Lead (20) makes contact with first electrode material (16) and lead (22) makes contact with second electrode material (18) by means of shunt (24). In the double-cell device (30) of FIG. 2, a first cell is comprised of an oxygen-ion conductive material (32) in combination with first electrode material (34) and second electrode material (36). The second cell of device (30) is formed by oxygen-ion conductive material (38), third electrode material (40) and forth electrode material (42). A cavity (44) is present between the two cells. Leads (46) and (48) make contact with first electrode material (34) and second electrode material (36) respectively, of the first cell, while leads (50) and (52) make contact with third electrode material (40) and forth electrode material (42) respectively, of the second cell. In the double-cell, one of the two cells is used as an oxygen pump element while the other one of them is used as an oxygen concentration (sensing) element. Using the double-cell, the oxygen concentration can be electrically measured by placing the oxygen sensor in the gas and applying an electric current through the oxygen pump element so as to pump oxygen out of the above-mentioned cavity to the outside atmosphere or the gas being measured, while allowing diffusion of oxygen into the cavity through the openings to the cavity, until for instance an oxygen concentration ratio between the cavity and the outside atmosphere or gas being measured reaches a certain stable value. The last mentioned oxygen concentration ratio is given by the oxygen concentration cell element as an output thereof, and the magnitude of the current applied to the oxygen pump element for pumping out oxygen corresponds to the oxygen concentration in the outside atmosphere or the gas being measured. This oxygen sensor uses the oxygen pump element and the oxygen concentration cell element, which are separately formed in this double-cell, so that the output from the oxygen sensor has an advantage in that the dependency of the output thereof on the temperature of the outside atmosphere or the gas being measured is low. In the single-cell device, the cell is used as an oxygen pumping element and the oxygen concentration is obtained by measuring the saturation pumping current as described, e.g., in *Fundamentals and Applications of Chemical Sensors*, D. Schuetzle and R. Hammerle, Editors, ACS Symposium Series 309, ACS, Washington, D.C., 1986, pps. 136–154.

Figure 4:
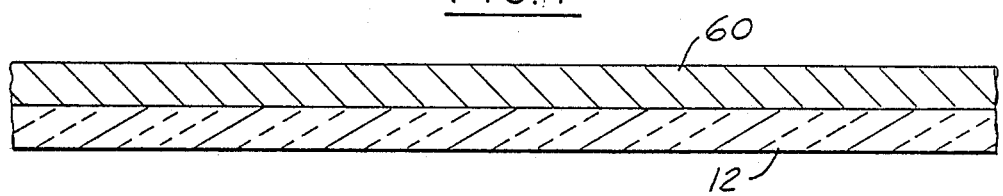

The first step of the method of the invention comprises providing a substantially uniform layer of a ceramic material having an inner surface in contact with a first surface of a substantially uniform layer of etchable material. The etchable material may be, e.g., a single crystal silicon wafer or a metal capable of being etched such as copper. The etchable material may be deposited on the layer of ceramic material or the ceramic material may be deposited on the etchable material. If the etchable material is silicon as shown in FIGS. 3–10, the ceramic material will preferably be deposited on a silicon wafer as shown in FIG. 4. If the method is being employed to form a single-cell device according to this invention, the ceramic material may be selected from non-oxygen-ion conductive ceramic materials such as alumina, spinel, and yttria, and from oxygen-ion conductive electrolytes such as $ZrO_2$, $Bi_2O_3$, $CeO_2$ and $ThO_2$ doped with well known additives such as $CaO$, $Y_2O_3$, and the like. In the embodiment of the method of this invention wherein it is intended to fabricate a double-cell device, this ceramic material would necessarily be an oxygen-ion conductive electrolyte material. It may be deposited, e.g., by chemical vapor deposition (CVD), flame spraying, sputtering, or evaporation. Such techniques as well as others for depositing ceramic type materials are well known to those skilled in the art.

Figure 5:
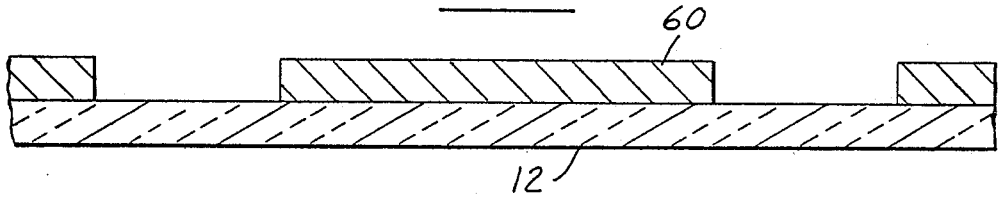
Figure 6:
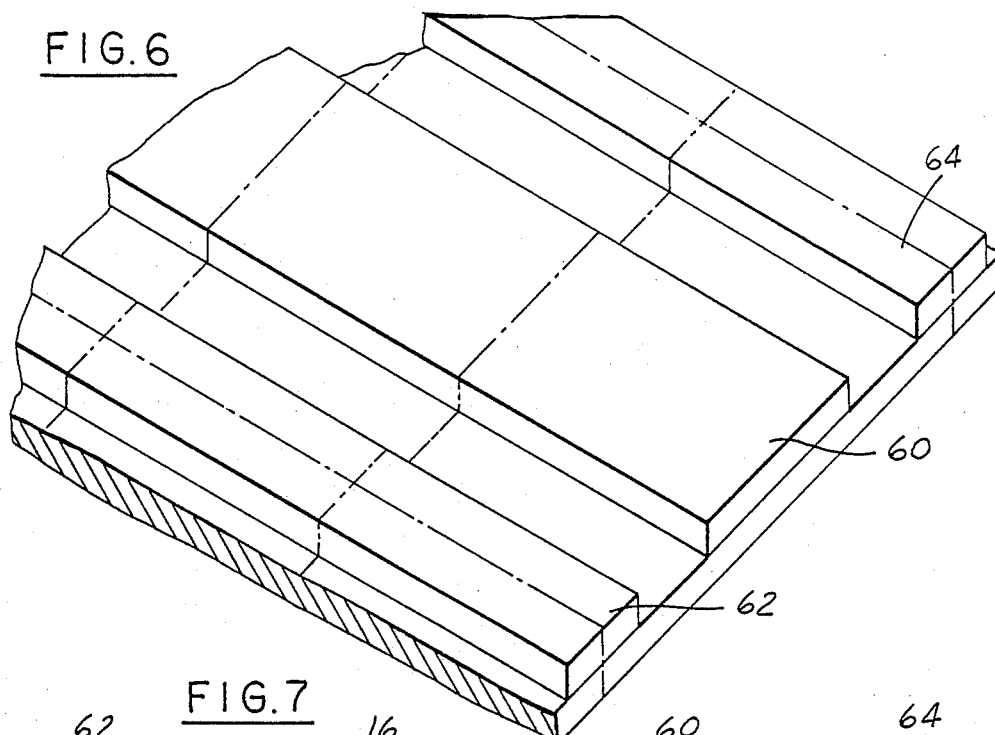

After forming the ceramic material/etchable material configuration, grooves are formed in a second surface opposite the first surface of the etchable material as shown in FIG. 5 in cross-section and in FIG. 6 in a perspective view thereof. This is done by etching away, in a predetermined pattern, substantially parallel, rectangular solid strips of the etchable material to expose, as a bottom surface of each said groove, correspondingly, substantially parallel rectangular portions of the inner surface of the layer of the ceramic material. This leaves at least a first set of substantially identical, substantially parallel, rectangular solid projecting strips (60) of the etchable material as shown in FIGS. 5 and 6. The etchable material may be etched by well established etching techniques known to those skilled in the art. Such techniques may involve masking those portions of the etchable material not to be etched with a photoresist material. If the etchable material is e.g, silicon or copper, they may be etched, e.g., by wet chemical etching techniques employing for example sodium hydroxide or $HF/HNO_3$ for the silicon and $HNO_3$ for copper, or by other suitable etching techniques. Selection of a suitable etching technique would be apparent to those skilled in the art in view of the present disclosure. Such techniques would depend in part on the material to be etched. Between ones of the first set of rectangular solid projecting strips may be ones of a second set of rectangular solid projecting strips, the width of each of the strips of the second set may be the same or different from the width of each of the strips of the first set. FIG. 6 depicts an embodiment wherein a projecting strip (60) of the first set of projecting strips is wider than projecting strips (62) and (64) of the second set.

Figure 7:
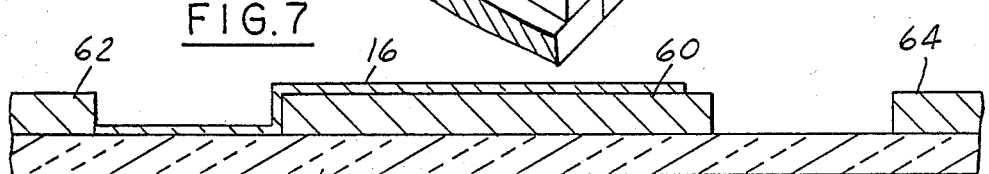

After forming the grooves as described above, a layer of first electrode material is deposited over at least a portion of each top surface of the rectangular solid projecting strips and at least a portion of one said grove bottom surface adjacent each of said rectangular solid projecting strips, the layer of the first electrode material extending laterally continuously from at least the middle of the top surface of each of the first set of rectangular solid projecting strips to at least about the middle of an adjacent groove bottom. The layer may extend longitudinally the length of the rectangular solid projecting strips and the adjacent grove bottom or extend over only certain portions thereof. If the layer of first electrode material extends over only certain portions, e.g., portions inside the second cut lines (b) of the grid pattern which are later made when the layered article is cut through, direct contact of non-covered portions of the layer of ceramic material (12) and corresponding portions of the layer of oxygen-ion conductive electrolyte material (14) is made. This allows for good adhesion of the two layers. In FIG. 7, it can be seen that the layer of first electrode material (16) is applied laterally continuously over a major portion of strip (60) of the first set of rectangular solid projecting strips over to one of the adjacent strips (62) of a second set of rectangular solid projecting strips. Covering in this manner, i.e., over to one of the adjacent strips, is generally used when each of the second strips of rectangular solid projecting strips is narrower than each of the first set of rectangular solid projecting strips as in the embodiment shown in FIG. 5 through FIG. 10. Covering in this manner would allow for lead contact with the electrode materials if the cutting through of the layered article is done down the middle of strips (62) and (64). If the method is being used to fabricate a single-cell device according to this invention, the first electrode layer may be deposited so as to cover even all of the surfaces of the projecting strips and the second surface of the etchable material, i.e., to act as a cover layer for the entire top surface of the configuration shown in FIG. 5. If a double-cell device is being fabricated according to the method of this invention, the layer of first electrode material (34) can extend laterally to at most about region (35) of the device of FIG. 2, so as to not contact the layer of third electrode material (40) shown therein. The electrodes are generally deposited in a thickness between about 0.2 micrometers and about 1 micrometer. This first electrode, as well as those discussed in the following text, are formed so as to have a microscopically porous structure permeable to gas molecules. Each is formed of a metal, individually selected from metals preferably of the platinum group such as Pt, Ru, Pd, Rh, Os and Ir, alloys of these platinum group metals and alloys of platinum group metals with a base metal. The electrode material may be applied by any known suitable technique including, e.g., electron-beam or sputtering techniques or by screen printing through appropriate masking. In the latter case, the electrode can be formed by applying a paste containing a powdered electrode material onto the surface to be covered by a screen printing technique, drying the resultant paste layer and thereafter firing the dried layer. Techniques for applying such materials are well known to those skilled in the art.

Figure 8:
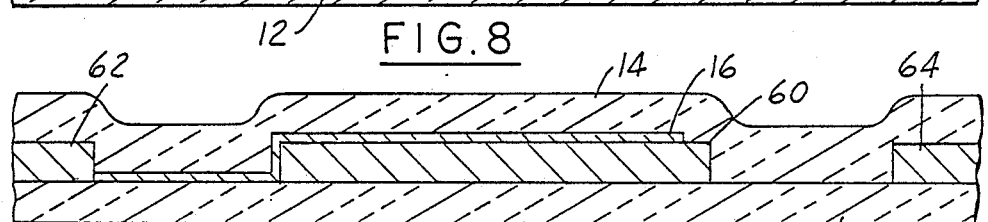
Figure 9:
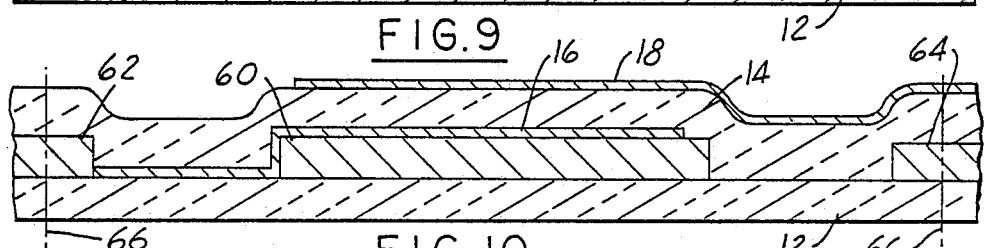
Figure 10:
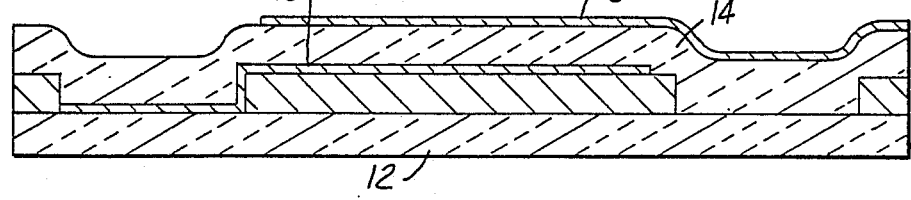

After depositing the first electrode, as shown in the configuration of FIG. 8, a cover layer of an oxygen-ion conductive electrolyte material (14) is deposited on the surfaces formed by the first electrode material (16) and any exposed (i) etchable material, e.g., silicon (60), (62) and (64), and (ii) the inner surface of the ceramic material (12). Accordingly, a layer of the electrolyte material provides a cover layer for the top of the entire top surface of the configuration shown in FIG. 7. Suitable oxygen-ion conductive electrolyte materials have been discussed above. Still other suitable materials will be apparent to those skilled in the art in view of the present disclosure.

Next, a layer of second electrode material (18), selected from the first electrode materials discussed above, is deposited over at least a portion of a top surface of the oxygen-ion conductive electrolyte material (14) to form a layered article. The second electrode material extends laterally continuously from at least the middle of the top surface of each of the first set of rectangular solid projecting strips to at least about the middle of an adjacent groove bottom. In FIG. 8, the second electrode layer is shown to extend laterally continuously over a major portion of the first set of rectangular solid projecting strips to at least the middle of the adjacent one of a second set of rectangular solid projecting strips. Since the second electrode layer extends laterally over to the middle of a strip of one of the second set of projecting strips, contact can be readily made between a lead and the electrode material in those embodiments wherein the the first cuts of the layered article will be made down the center of the second set of projecting strips. This second electrode layer could be deposited so as to extend over (cover) the entire surface of the layer of the oxygen-ion conductive ceramic material (14) of FIG. 9.

Thereafter, the layered article is cut through in planes perpendicular to the plane of the layered article in a grid pattern comprising (a) cuts between adjacent ones of the first set of the rectangular solid projecting strips and (b) cuts along chosen lines perpendicular to the first cuts (a) to produce a plurality of individual structures. This cutting through exposes for each one a first and second electrode material. Layered article could be, e.g., cut down the center of the grooves adjacent to each of the strips of the first set of rectangular solid projecting strips or, when the second set of rectangular solid projecting strips has been formed, as described above, generally would be cut down the center of the second set of rectangular solid projecting strips as shown by the broken lines in FIG. 6. This cutting may be done, e.g., by a dicing machine. Other suitable means to effect cutting of the layered article will be apparent to those in the art in view of the present disclosure.

Next, any etchable material remaining in the individual structures is etched away, e.g., by means of an etching solution, to form the devices. Etching techniques have been discussed above which may be suitably employed to etch any remaining etchable material from the individual structures. A cavity is formed in a device when the etchable material remaining in the individual structure is etched away.

In the case of forming a double-cell device according to the method of this invention, before the deposition of the ceramic material (38), FIG. 2, a layer of third electrode material (40), is deposited over at least a portion of the first surface of the etchable material, the layer of third electrode material extending laterally continuously from at least the middle of the top surface of each of the first set of the rectangular solid projecting strips to at least about the middle of an adjacent groove bottom. If the layer of third electrode material extends over only certain portions, e.g., portions inside the second cut lines of the grid pattern to be made when the layered article is cut through, more direct contact of non-covered portions of the layer of ceramic material (38) and corresponding portions of the layer of oxygen-ion conductive electrolyte material (32) is made. This allows for good adhesion of these two layers. The layers of first and third electrode materials are deposited so as to avoid contact at region (39) shown in FIG. 2. In the double-cell device, the method further comprises depositing, prior to cutting through the layered article, a layer of fourth electrode material (42) on at least a portion of an exposed surface of the ceramic material (38) (which in a double-cell device is oxygen-ion conductive electrolyte material), the layer of forth electrode material extending laterally continuously from at least the middle of each of the first set of the rectangular solid projecting strips to at least about the middle of an adjacent groove bottom. As with the layer of first electrode material, the layer of third electrode material is shown in FIG. 2 as extending laterally continuously over a major portion of the etchable material and to at least the middle of an adjacent one of the second set of rectangular solid projecting strips. As with the layer of the second electrode material extending over the ceramic material, the layer of the fourth electrode material (42) can extend over even the entire surface of the ceramic material (38) (which in the double-cell device is oxygen-ion conductive electrolyte material).

The dimensions of the device components, i.e., the width of the rectangular solid projecting strips and the grooves, as well as the thickness of the ceramic layer, of the oxygen-ion conductive electrolyte layer and the etchable material can vary and will depend, for example on the desired size of the final device as well as the type of device, i.e., a single-cell device vs a double-cell device. In a single-cell device, the oxygen-ion conductive electrolyte material (working) layer (14) between electrode layers (16) and (18), FIG. 1, would optimally be deposited as thin as possible so as to provide a device with a relatively low impedance. In such a single-cell device the ceramic layer (12) would generally be thicker than the working layer (14) so as to provide structural support to the device. In a double-cell device, since both layers (32) and (38) are working layers, they both should optimally be as thin as possible and preferably be of the same thickness, while being thick enough to provide structural integrity to the structure. The larger the size of the cavity, the faster the response time of the device and the less likely the cavity might become partially obstructed with foreign material from exhaust gases (if the device is used to measure such). However, the larger the opening the larger the current required to operate the device, such larger currents being less desirable. Therefore, the cavity size as well as the size of layers (12), (14), (32), and (38) are optimized in view of such considerations. Generally, in the devices shown in FIGS. 1 and 2, when the device width from cut end to cut end is about 2 mm (according to a device as shown in FIG. 1), the thickness of the ceramic layer and the oxygen-ion conductive electrolyte layer is each between about 0.1 and 0.5 mm. The height of the cavity opening is between about 0.03 and about 0.5 mm, preferably about 0.1 mm, for a device of the dimensions described above. Selection of the optimal dimensions for each of the component layers of the device will be apparent to those skilled in the art in view of the present disclosure. While in the single-cell device the layers (12) and (14) may be of different materials, it is preferred that they be of the same oxygen-ion conducting electrolyte material for optimal adhesion between these layers since this would allow for the same coefficient of expansion, etc., between such layers. This is also the case with the double-cell device.

For use of devices, leads will be connected to the electrode materials. This may be done in various ways including those shown in the figures herein. Still other ways for attaching the leads to the electrode materials of the device would be apparet to those in the art in view of the present disclosure.

In view of this disclosure, many modifications of this invention will be apparent to those skilled in the art. It is intended that all such modifications which fall within the true scope of this invention be included within the terms of the appended claims.

We claim:

1. A method for making planar oxygen pumping devices by a batch technique, which method comprises:

providing a substantially uniform layer of a ceramic material having an inner surface in contact with a first surface of a substantially uniform layer of etchable material;

then forming grooves in a second surface opposite said first surface of said etchable material by etching away, in a predetermined pattern, substantially parallel, rectangular solid strips of said etchable material to expose, as a bottom surface of each said groove, corresponding, substantially parallel rectangular surface portions of the inner surface of said layer of ceramic material, leaving at least a first set of substantially identical, substantially parallel, rectangular solid projecting strips of said etchable material;

then depositing a layer of first electrode material over at least on a portion of a top surface of each said rectangular solid projecting strip and at least a portion of one said groove bottom surface adjacent each said rectangular solid projecting strip, said layer of first electrode material extending laterally continuously from at least the middle of the top surface of each of said first set of rectangular solid projecting strips to at least about the middle of said adjacent groove bottom;

then depositing a cover layer of an oxygen-ion conductive electrolyte material over the first electrode material and any exposed (i) etchable material and (ii) said inner surface of said ceramic material;

then depositing a layer of second electrode material over at least a portion of a top surface of said oxygen-ion conductive electrolyte material to form a layered article, said layer of said second electrode material extending laterally continuously at least from the middle of the top surface of each of said first set of said rectangular solid projecting strips to at least about the middle of an adjacent groove bottom;

then cutting through said layered article perpendicular to the plane of said layered article in a grid pattern comprising (a) cuts between adjacent ones of said first set of rectangular solid projecting strips to expose for each one first and second electrode material and (b) cuts along lines perpendicular to said first cuts to produce a plurality of individual structures; and then etching away the remaining etchable material from said individual structures to form said devices.

2. The method according to claim 1, wherein said oxygen-ion conductive electrolyte material is selected from doped (a) zirconium oxide, (b) cerium oxide, (c) thorium oxide and (d) bismuth oxide.

3. The method according to claim 1, wherein said first and said second electrode materials are independently selected from platinum group metals and alloys thereof.

4. The method according to claim 1, wherein said etchable material is silicon having a substantially uniform thickness between about 0.03 mm and 0.5 mm.

5. The method according to claim 1, wherein said ceramic material is selected from alumina and spinel.

6. The method according to claim 1, wherein said ceramic material is selected from doped (a) zirconium oxide, (b) cerium oxide, (c) thorium oxide and (d) bismuth oxide.

7. The method according to claim 1, wherein said first cut comprises cutting through the middle of said grooves adjacent each of said first set of rectangular solid projecting strips along a line parallel to said strips.

8. The method according to claim 1, wherein said forming of grooves leaves a second set of substantially identical, substantially parallel rectangular solid projecting strips of etchable material which are parallel to said first set of rectangular solid projecting strips, the strips of said first set of rectangular solid projecting strips alternating with the strips of said second set of rectangular solid projecting strips, wherein said layer of said first electrode material extends laterally continuously at least from the middle of the top surface of each of said first set of rectangular solid projecting strips to an opposite longitudinal edge of an adjacent groove bottom surface, wherein said layer of said second electrode material extends laterally continuously at least from the middle of the top surface of each of said first set of rectangular solid projecting strips to about the middle of an adjacent one of said second set of rectangular solid projecting strips, and wherein said first cuts through said layered article are through about the middle of each strip of said second set of rectangular solid projecting strips.

9. The method according to claim 1, werein said ceramic material is an oxygen-ion conducting electrolyte and, prior to depositing said ceramic material, said method further comprises depositing a layer of third electrode material on at least a portion of said first surface of said etchable material, said layer of said third electrode material extending laterally continuously at least from the middle of the top surface of each of first set of said rectangular solid projecting strip to at least about the middle of an adjacent groove bottom, said first and said second electrode materials being deposited so as to avoid contact with each other, and prior to cutting through said layered article, depositing a layer of forth electrode material on an exposed surface of said ceramic material, said layer of forth electrode material extending laterally continuously at least from the middle of each of said first set of said rectangular solid projecting strips to at least about the middle of an adjacent grove bottom.

10. The method according to claim 9, wherein said first cuts are through said middle of said grooves adjacent each of said first set of rectangular solid projecting strips along a line parallel to said strips.

11. The method according to claim 9, wherein said forming of said grooves leaves a second set of substantially identical, substantially parallel rectangular solid projecting strips of etchable material which are parallel to said first set of rectangular solid projecting strips and each of the strips of said first set of rectangular solid projecting strips alternates and is adjacent to one of the strips of said second set of rectangular solid projecting strips, wherein said layer of said first electrode material extends laterally continuously at least from the middle of the top surface of each of said first set of said rectangular solid projecting strips to a remote end of an adjacent groove bottom, wherein said layer of said second electrode material extended laterally continuously at least from the middle of the top surface of each of said first set of said rectangular solid projecting strips to about the middle of an adjacent one of said second set of said rectangular solid projecting strips, and wherein said first cuts are through about the middle of each strip of said second set of rectangular solid projecting strips along a line parallel to said strips.

12. The method according to claim 9, wherein said ceramic material is selected from doped (a) zirconium oxide, (b) cerium oxide, (c) thorium oxide and (d) bismuth oxide.

13. A device fabricated according to the method of claim 1.

14. A device fabricated according to the method of claim 8.

15. A device fabricated according to the method of claim 9.

16. A device fabricated according to the method of claim 11.

* * * * *